United States Patent [19]

Bigge et al.

[11] Patent Number: 5,668,121
[45] Date of Patent: Sep. 16, 1997

[54] GLUTAMATE (NMDA) RECEPTOR ANTAGONISTS

[75] Inventors: Christopher Franklin Bigge; James Jia-He Li, both of Ann Arbor, Mich.

[73] Assignee: Warner-Lambert Company, Morris Plains, N.J.

[21] Appl. No.: 534,079

[22] Filed: Sep. 15, 1995

Related U.S. Application Data

[62] Division of Ser. No. 271,961, Jul. 8, 1994, Pat. No. 5,489,717.

[51] Int. Cl.$^6$ .............................. A61K 31/66; C07F 9/22; C07F 9/02; C07C 229/00
[52] U.S. Cl. .................. 514/114; 514/119; 562/11; 560/38; 558/166
[58] Field of Search ........................ 562/11; 558/166; 560/38; 514/114, 119

[56] References Cited

U.S. PATENT DOCUMENTS

| | | | |
|---|---|---|---|
| 4,657,899 | 4/1987 | Rzeszotarski et al. | 514/120 |
| 4,761,405 | 8/1988 | Rzeszotarski et al. | 514/114 |
| 4,918,064 | 4/1990 | Cordi et al. | 514/114 |
| 5,100,654 | 3/1992 | Pawelek et al. | 424/59 |
| 5,162,311 | 11/1992 | Herrling et al. | 514/110 |
| 5,175,153 | 12/1992 | Bigge et al. | 514/114 |
| 5,190,921 | 3/1993 | Roques et al. | 514/17 |
| 5,200,546 | 4/1993 | Burke, Jr. et al. | 558/190 |
| 5,238,958 | 8/1993 | Johnson et al. | 514/533 |
| 5,395,827 | 3/1995 | Rzeszotarski et al. | 514/114 |

FOREIGN PATENT DOCUMENTS

| | | |
|---|---|---|
| 488959A2 | 6/1992 | European Pat. Off. . |
| 93/25561 | 12/1993 | WIPO . |

OTHER PUBLICATIONS

Scatton, B., *Fundam Clin Pharmacol*, 1993, 7, 389–400.
Lipton, S.A., *TINS* 1993, 16:12, 527–532.
Bigge, C.F., et al., *Current Opinion in Therapeutic Patents*, 1993, 951–989.
Bigge, C.F., *Biochemical Pharmacology*, 1993, 45:8, 1547–1561.
Lipton, S.A., et al., *New England J of Medicine*, 1994, 330:9, 613–622.
Ortwine, D.F., et al., *J Med. Chem*, 1992, 35, 1345–1370.
Benveniste, M., et al., *Molecular Pharmacology*, 1992, 42:4, 679–686.
Klockgether, T., et al., *Annals of Neurology*, 1993, 34:4, 585–593.
Francis P.T., et al., *J of Neurochemistry*, 1993, 60:5, 1589–1604.
Dorville, A., et al., *J Med Chem*, 1992, 35:14, 2551–2561.
Bigge, C.F., et al., *J Med Chem*, 1989, 32:7, 1580–1590.
Bigge, C.F., et al., *J Med Chem*, 1989, 32:12, 2583.
Mueller, W., et al., *Helvetica Chimica Acta*, 1992, 75:855–864.
Sosnowski, M., *Support Care Cancer*, 1993, 1:79–88.

*Primary Examiner*—Joseph Conrad
*Attorney, Agent, or Firm*—Elizabeth M. Anderson

[57] ABSTRACT

Novel naphthyl-substituted α-amino acid derivatives, pharmaceutical compositions containing the same and a method of using the same, for the blockade of aspartate and glutamate receptors, are described. Novel intermediates of the napthyl-substituted α-amino acid derivatives are disclosed.

14 Claims, No Drawings

GLUTAMATE (NMDA) RECEPTOR ANTAGONISTS

This is a Divisional Application of U.S. Ser. No. 08/271,961 filed Jul. 8, 1994, U.S. Pat. No. 5,489,717.

BACKGROUND OF THE INVENTION

1. Field of the Invention

This invention is related to naphthyl-substituted α-amino acid derivatives that are active as excitatory amino acid receptor antagonists acting at glutamate receptors, specifically N-methyl-D-aspartate ("NMDA") receptors. The invention also relates to the use of those α-amino acid derivatives as neuroprotective agents for treating cerebral ischemia caused by cerebral trauma, stroke, hypoglycemia, heart attack and surgery; as a treatment for anxiety and schizophrenia; as an analgesic and adjunct to opioid analgesia therapy; and to treat chronic neurodegenerative disorders such as Huntington's Disease, ALS, Parkinsonism, and Alzheimer's Disease.

2. Related Background Art

Various α-amino acid derivatives, such as phenylalanine derivatives, have been disclosed as NMDA receptor antagonists. U.S. Pat. No. 5,175,153 discloses 3-(phosphonomethyl)phenylalanine as an NMDA receptor antagonist and generically discloses compounds of the formula

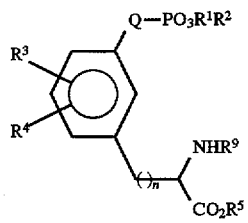

wherein: n is 0, 1, or 2; $R^1$, $R^2$ and $R^5$ are independently hydrogen or a pharmaceutically acceptable labile ester or amide residue; $R^3$ and $R^4$ are independently hydrogen, hydroxy, lower alkyl optionally substituted by hydroxy or methoxy, aryl, aralkyl, lower alkoxy, $R^{10}S(O)_{0-1}(CH_2)_q$ wherein q is 0, 1, or 2 and $R^{10}$ is lower alkyl, halogen, trifluoromethyl, or $R^3$ and $R^4$ when on adjacent ring carbons are together —CH=CH—CH=CH—; $R^9$ is a hydrogen or a protective group; Q is —$(CH_2)_m$—, —(CH=CH)—, —$CH_2$—(CH=CH)—, or —(CH=CH)—$CH_2$— wherein m is 0, 1, 2 or 3. This reference does not disclose the naphthyl-substituted α-amino acid derivatives of the present invention or their unexpectedly improved NMDA receptor antagonism.

Phenylalanine derivatives having a phenyl or substituted phenyl group attached to C-1 of the primary phenyl ring are disclosed in U.S. Pat. No. 5,162,311. [See also, Mueller, et al., Helv. Chim. Acta, 75(3), 855–64 (1992)]. This patent specifically discloses (+)-α-amino-3-(5-phosphonomethyl-[1,1'-biphenyl]-3-yl)propanoic acid. The claims of U.S. Pat. No. 5,162,311 are, however, specifically limited to an unsubstituted or monosubstituted phenyl ring and, thus, do not suggest naphthyl-substituted phenylalanine derivatives.

U.S. Pat. No. 4,918,064 discloses phenylglycine analogs that may be aryl substituted. However, naphthyl substituents are not exemplified, and the phenyl ring is specifically substituted at C-4 instead of C-3.

None of the aforementioned references disclose or suggest the unexpected improvement in NMDA receptor antagonist activity of the naphthyl-substituted α-amino acid derivatives of this invention, or the discovery that the compounds of this invention are substrates to a neutral amino acid transporter which may enhance their access into the central nervous system.

It is particularly evident from the literature that most potent NMDA receptor antagonists have an unnatural (R)-configuration of the α-amino acid moiety. Amino acids with an unnatural (R) configuration are neither able to utilize neutral amino acid transport systems for absorption systemically, nor can they utilize transport systems in endothelial cells of the blood brain barrier to enhance their transport into the central nervous system (CNS). The naphthyl-substituted α-amino acid derivatives of this invention were designed specifically to enhance their access into the CNS via neutral amino acid transport systems. Without being held or bound to any theory, it is believed that the naphthyl-substituted α-amino acid derivatives of the present invention act as transport substrates, which may help to explain their unexpected in vivo potency.

Among excitatory amino acid receptor antagonists recognized for usefulness in the treatment of disorders are those that block NMDA receptors. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A). A recent review describes most of the recent structural types of NMDA receptor antagonists [C. F. Bigge and T. C. Malone, Curr. Opin. Ther. Pat., 951–989 (1993)].

An object of this invention is to provide novel naphthyl-substituted α-amino acid derivatives which are unexpectedly potent NMDA antagonists. The improved potency of these compounds advantageously allows for the administration of lower doses of the compounds which may result in the reduction of side effects associated with NMDA antagonist therapy.

A further object of this invention is to provide a pharmaceutical composition containing an effective amount of the naphthyl-substituted α-amino acid derivatives to treat cerebrovascular disorders responsive to blocking glutamate and NMDA receptors, and a pharmaceutically acceptable carrier.

Another object of this invention is to provide a method of treating disorders responsive to the antagonism of glutamate or aspartate receptors in a human by administering a pharmaceutically effective amount of the naphthyl-substituted α-amino acid derivatives of this invention.

A further object of this invention is directed to novel intermediates of the napthyl-substituted α-amino acid derivaties of this invention.

SUMMARY OF THE INVENTION

The present invention is directed to compounds of the formula (I):

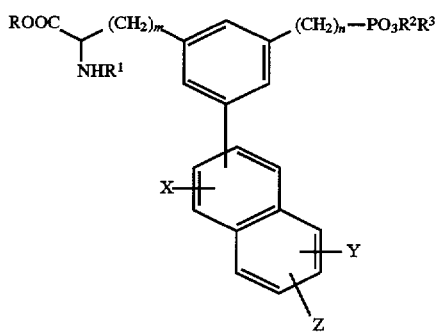

(I)

wherein m and n are independently an integer of 0 to 3; R, $R^2$ and $R^3$ are independently hydrogen or a pharmaceutically acceptable labile ester or amide residue; $R^1$ is hydrogen or a protective group; and X, Y and Z are independently hydrogen, halogen, amino, hydroxy, hydroxyalkyl having 1 to 6 carbon atoms, haloalkyl having 1 to 6 carbon atoms, cyano, nitro, alkyl having 1 to 6 carbon atoms, cycloalkyl, aryl, aralkyl, aminoalkyl having 1 to 6 carbon atoms or alkoxy having 1 to 6 carbon atoms.

The compounds of this invention include pharmaceutically acceptable salts, solvates and hydrates of the compounds of formula I. Also included are the tautomeric forms and isomeric forms of the compounds of formula I, including diastereomers and enantiomers.

A preferred class of compounds of formula I of this invention includes those compounds where m and n are 1, i.e., the phenylalanine class of compounds. It is also preferred that the C-1 position of the naphthalenyl group is attached to the phenyl ring of the α-amino acid derivative of formula I. Highly preferred compounds of this invention include, for example, the L and DL forms of 3-(1-naphthalenyl)-5-(phosphonomethyl)-L-phenylalanine.

The instant invention is also related to a pharmaceutical composition containing the compound defined by formula I in an amount effective to treat cerebrovascular disorders responsive to the blockade of glutamate and NMDA receptors, and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's disease, ALS, Parkinsonism and Alzheimer's disease. The pharmaceutical composition of this invention may also be employed as an analgesic or as an adjunct to opioid analgesia therapy.

The invention further relates to a method of treating cerebrovascular disorders responsive to antagonism of glutamate and NMDA receptors by administering a compound of above-defined formula I in a unit dosage form.

This invention is further directed to novel intermediates prepared during the preparation of the napthyl-substituted α-amino acid derivatives of this invention. The novel intermediate compounds are represented by the formula:

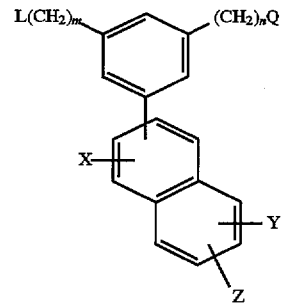

wherein (a) m and n are independently an integer of 0 to 3; (b) Q is selected from a group represented by hydrogen, Br or; $PO_3Et_2$; (c) L is selected from a group represented by hydrogen, Br, or by the formulae

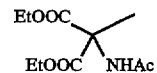

or

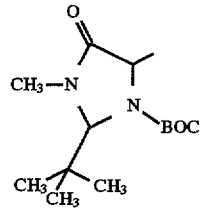

and (d) X, Y and Z are independently hydrogen, halogen, amino, hydroxy, hydroxyalkyl having 1 to 6 carbon atoms, haloalkyl having 1 to 6 carbon atoms, cyano, nitro, alkyl having 1 to 6 carbon atoms, cycloalkyl, aryl, aralkyl, aminoalkyl having 1 to 6 carbon atoms or alkoxy having 1 to 6 carbon atoms, provided L and Q are both not hydrogen.

Preferred intermediate compounds of this invention include those selected from group consisting of 1-[3-(bromomethyl)-5-methylphenyl]naphthalene, 2-[3-(Bromomethyl)-5-methylphenyl]naphthalene, diethyl [3-methyl-5-(1-naphthalenyl)phenyl] methylphosphonate, diethyl [3-methyl-5-(2-naphthalenyl)phenyl] methylphosphonate, diethyl [3-(bromomethyl)-5-(1-naphthalenyl)phenyl] methylphosphonate, diethyl [3-bromomethyl)-5-(2-naphthalenyl)phenyl] methylphosphonate, diethyl(acetylamino)[[3-[(diethoxyphosphinyl)methyl]-5-(1-naphthalenyl)-phenyl] methylpropanedioate, diethyl (acetylamino) [[3-[(diethoxyphosphinyl) methyl]-5-(2-naphthalenyl)phenyl] methyl] propanedioate, 1,1-dimethylethyl(2S-trans)-5-[[3-(diethoxyphosphinyl)methyl]-5-(1-naphthalenyl) phenyl] methyl]-2-(1,1-dimethylethyl)-3-methyl-4-oxo-1-imidazolidinecarboxylate and 1,1-dimethylethyl (2S-trans)-5-[[3-(diethoxyphosphinyl)methyl]-5-(2-naphthalenyl) phenyl]methyl]-2-(1,1-dimethylethyl)-3-methyl-4-oxo-1-imidazolidinecarboxylate.

DETAILED DESCRIPTION OF THE PREFERRED EMBODIMENTS

The naphthyl-substituted α-amino acid derivatives of this invention are represented by previously defined formula I. In the context of this invention, the phrase pharmaceutically acceptable labile ester residues means an ester residue of the esterified carboxy group or the esterified phosphono group of formula I, preferably a carboxylic acid or phosphono acid prodrug ester that may be convertible under physiological conditions to free carboxy or phosphono acid groups. Exemplary pharmaceutically acceptable esterified carboxy and phosphono groups are listed in U.S. Pat. No. 5,175,153, the disclosure of which is incorporated by reference herein as if fully set forth.

Within the context of this invention the phrase "amide residue" means that either the carboxy or phosphono substituent may include those amides known by those skilled in the art to be useful as prodrugs.

When X, Y or Z are alkyl it is preferred that the alkyl is a straight chain or branched alkyl having one to six carbon atoms. Exemplary lower alkyl groups include, for example, methyl, ethyl, propyl, butyl, pentyl, hexyl and isomers thereof. Similarly, when X, Y or Z are alkoxy, it is preferred that the alkoxy is an alkoxy having one to six carbon atoms. It is most preferred that X, Y and Z are hydrogen.

It is further preferred that m and n are 1 and that the naphthyl group is attached to the phenyl ring at the C-1 or C-2 carbon. It is most preferred that the naphthyl group is attached to the phenyl ring at the C-1 carbon.

The naphthyl-substituted α-amino acid derivatives of formula I can be prepared using conventional reaction techniques and schemes readily understood by those skilled in the art. Moreover, the starting materials are either readily available or can be prepared by known methods.

As an example, the naphthyl-substituted phenylalanine derivatives of this invention can be prepared in a conventional manner as illustrated below by equations 1–7. The naphthalene ring may be generically substituted as set forth in formula I. Such naphthalene derivatives are known in the chemistry literature and accessible by processes known to one skilled in the art. The process sequence set forth herein does not present an exact sequence of reactions by which the compound must be made; that is, the sequence of reactions can be rearranged in several ways to reach the target molecule. For example, the amino acid-containing moiety could be attached prior to phosphonate formation, etc. and the biaryl coupling reaction does not need to be the first reaction in the sequence. The alteration of such sequences is well understood by those skilled in the art.

Naphthalene boronic acids are available by generation of a Grignard reagent followed by quenching with a trialkylborate. Hydrolysis of the borate ester proceeds to the product (Eq. 1).

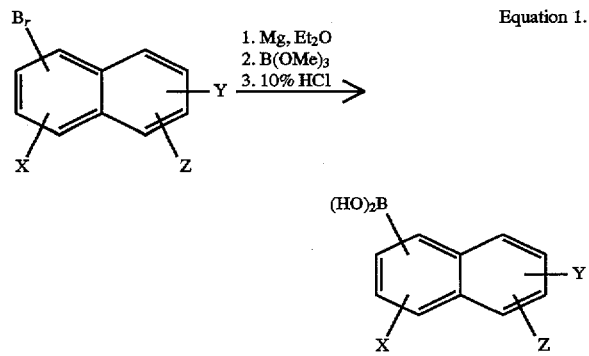

Several methods utilizing palladium (II) or palladium (0) as catalyst are useful for effecting unsymmetrical biaryl couplings including the Suzuki coupling reaction employed herein (Eq. 2).

Still coupling using aryl tin compounds and palladium catalysis are also useful and can be used with equal success. Other catalysts that can be substituted include copper and nickel catalysts. The solvent can also be varied: DMF, tetrahydrofuran, alcohol(s), ethyl acetate and other organic solvents can be used. The temperature of the reaction is generally between 0° C. and 200° C.

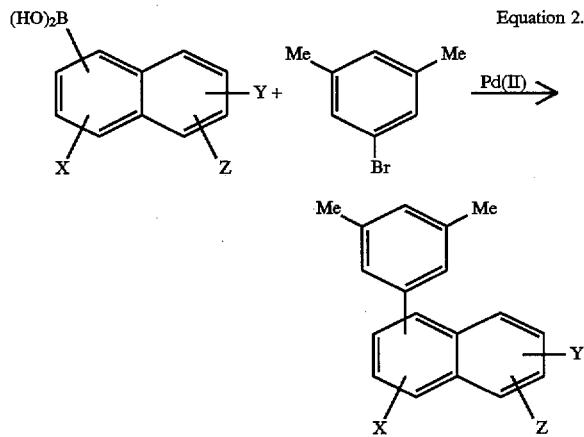

In Eq. 3 the monobromide is formed, along with dibromo and tribromo byproducts, by oxidative bromination using N-bromosuccinimide (NBS) in carbon tetrachloride in the presence of a trace amount of a radical initiator such as benzoyl peroxide or AIBN (2,2'-azobisisobutyronitrile). Other chlorinated solvents can be substituted. Alternative methods of preparation of the bromo derivative, or an equivalent electrophile, such as a tosylate, mesylate or the like, can be effected by means known to those skilled in the art. For example, the methyl groups could be oxidized and reduced to an alcohol, and then subsequently derivatized to a leaving group which could react in a manner similar to the bromide.

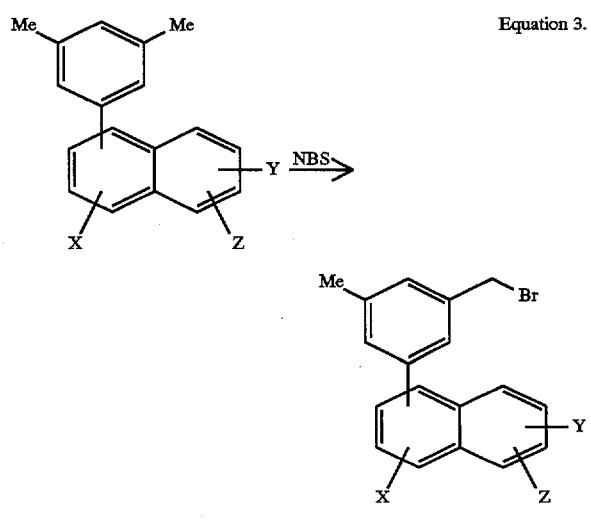

The diethylphosphonate is obtained by an Arbuzov reaction using a trisubstituted phosphite as a nucleophile to displace the bromide (or other leaving group, Eq. 4). Alternatively, sodium diethylphosphonate is a complementary procedure that may be used. In extreme cases, it may be necessary to react the electrophile with a phosphine derivative and oxidize to the phosphonate.

Equation 4.

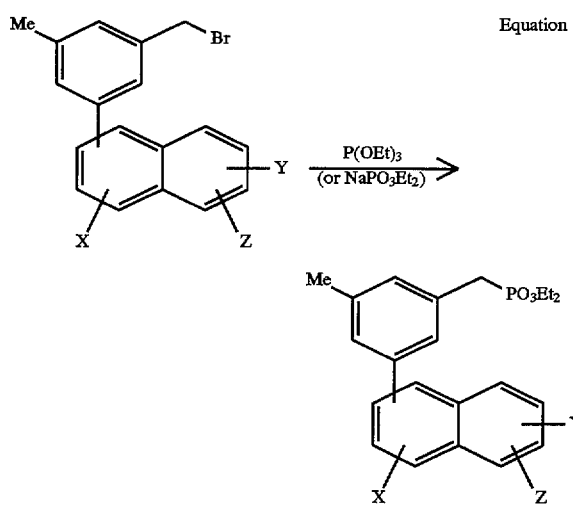

Equation 5 uses similar methodology described in equation 3. Similarly, other brominating agents can be used, or other leaving groups, such as tosylates or mesyleates, etc. can be substituted for the bromine and give a reactive product that can participate in substitution reactions.

Equation 5.

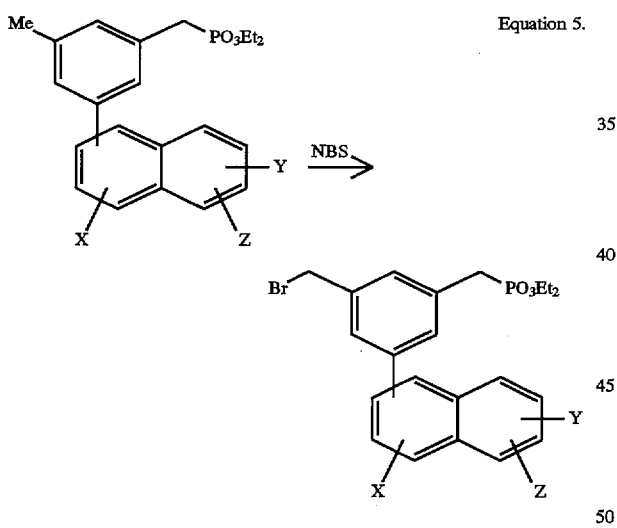

Chiral auxiliary groups are known which react in a displacement reaction with electrophiles to produce stereospecific intermediates that lead to α-amino acid derivatives with high enantioselectivity. Several chemists including Evans, Corey, Myers, Hegedus, Seebach, and others have developed various chiral auxiliaries that are known to one skilled in the art and that can be used for the enantioselective preparation of α-amino acids. In this case (Eq. 6) an auxiliary of Seebach is used as its enolate to displace the bromide and produce in high enantiomeric purity the desired adduct. Alternatively, there are many other reagents, including diethyl acetamidomalonate which are useful for the preparation of racemic α-amino acids.

Equation 6.

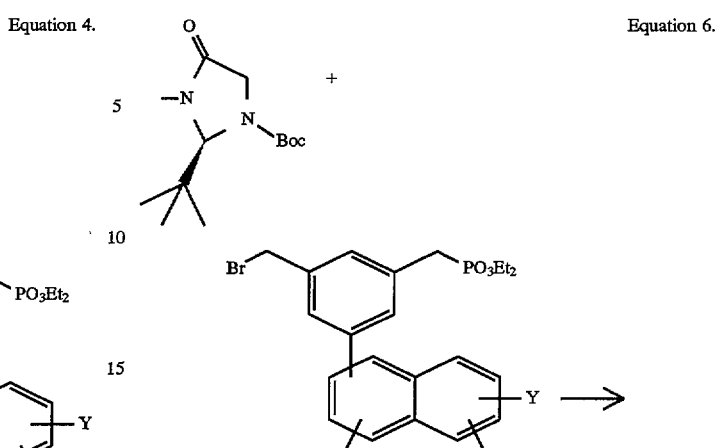

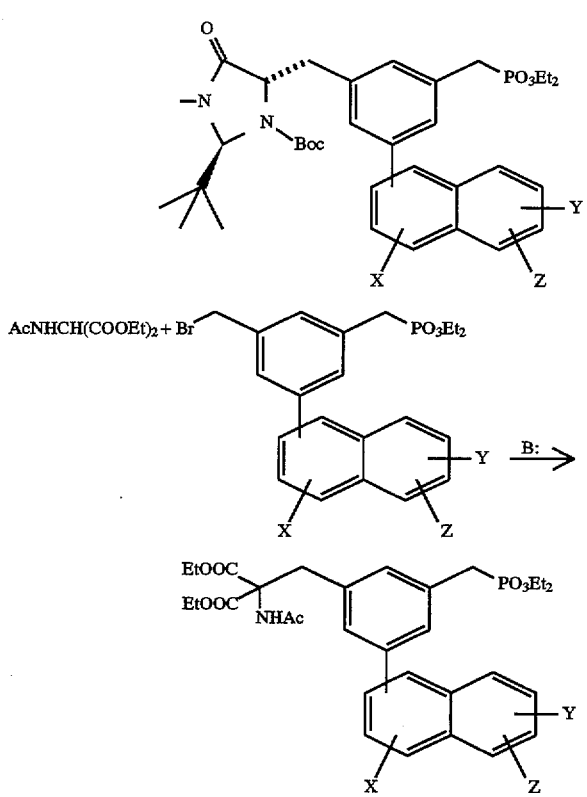

Deprotection of the fully protected α-amino acid derivative can be effected by treatment with 6N HCl (Eq. 7). In some instances, sequential deprotection strategies may be required when the substrate or product is unable to withstand strongly acidic conditions. Bromotrimethylsilane and iodotrimethylsilane can be used interchangeably to deprotect the phosphonate esters. Mild oxidative hydrolysis of the imidazolidinone can be accomplished. Racemic amino acid derivatives can be resolved by standard methods to the pure enantiomers. For example, resolution of the enantiomers can be accomplished by: (1) preparing a chiral ester or amide, followed by chromatography; (2) selective crystallization using a chiral salt; or (3) chromatography of the racemic mixture on a chiral column.

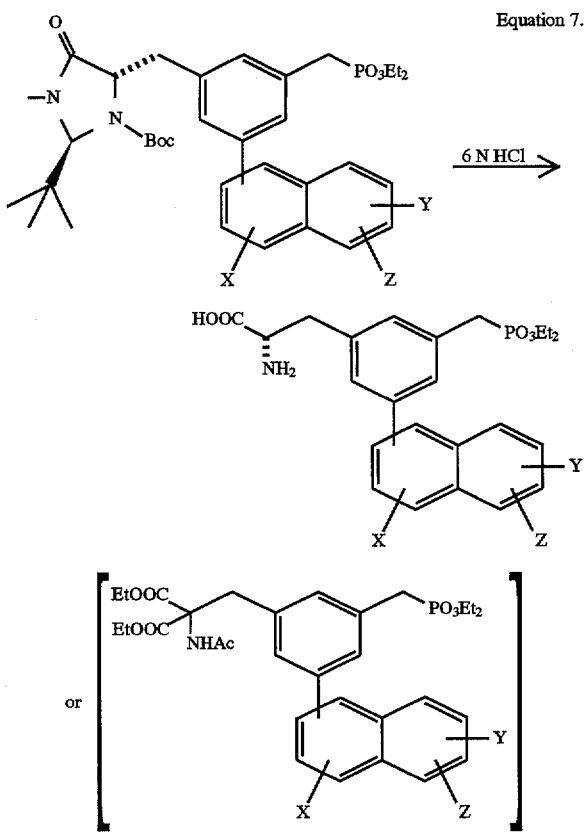

Equation 7.

Other manners, variations or sequences of preparing the compounds of Formula I will be readily apparent to those skilled in the art.

The compounds of formula I may be useful in the free base form, in the form of base salts where possible, and in the form of addition salts, as well as in the free acid form. All these forms are within the scope of this invention. In practice, use of the salt form amounts to use of the base form. Pharmaceutically acceptable salts within the scope of this invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like respectively, or those derived from bases such as suitable organic and inorganic bases. Examples of pharmaceutically acceptable base addition salts with compounds of the present invention include organic bases which are nontoxic and strong enough to form such salts. These organic bases and the use thereof are readily understood by those skilled in the art. Merely for the purpose of illustration, such organic bases may include mono-, di-, and trialkylamines, such as methylamine, diethylamine and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl) aminoethane; and the like.

The acid addition salts of the basic compounds may be prepared by dissolving the free base of the compound of formula I in aqueous or aqueous alcohol solution or other suitable solvents containing the appropriate acid or base and isolating the salt by evaporating the solution, or by reacting the free base of the compound of formula I with an acid as well as reacting the compound of formula I having an acid group thereon with a base such that the reactions are in an organic solvent, in which case the salt separates directly or can be obtained by concentration of the solution.

The compounds of this invention contain one or more asymmetric carbon atoms. Therefore, the invention includes the individual stereoisomers and mixtures thereof as well as the racemic compounds. The individual isomers may be prepared or isolated by methods known in the art.

The compounds of the invention exhibit pharmacological activity and are, therefore, useful as pharmaceuticals. In particular the compounds exhibit central nervous system activity.

Receptor binding experiments were performed using synaptosomal membrane from rat cortex according to means described in the literature. [$^3$H]-Glutamate (agonist) and [$^3$H]-CGP 39653 (antagonist) are ligands used in the binding experiments, and displacement of the radiolabeled ligand by one of the naphthyl-substituted α-amino acid compounds of the invention in competition experiments demonstrated that the compounds bind at the glutamate recognition site of the NMDA receptor. The compounds of this invention were found to have potent affinity (defined by their ability to displace 50% of the radioligand) in the range of a few nM to 10 μM for the NMDA recognition site in both receptor binding assays.

The most preferred compound of this invention, 3-(1-naphthalenyl)-5-(phosphonomethyl)-L-phenylalanine, exhibited a 4 nM affinity in a [$^3$H]-glutamate binding assay and a 0.008 μM affinity in a [$^3$H]-CGP binding assay. In comparison, the prior art compound substituted with a phenyl group intead of a naphthyl group, i.e., (+)-α-amino-3-(5-phosphonomethyl-[1,1'-biphenyl]-3-yl)propanoic acid exhibited a 115 nM affinity in a [$^3$H]-glutamate binding assay and a 0.098 μM affinity in a [$^3$H]-CGP binding assay. Moreover, Bigge, et al., J. Med. Chem., 32 1580 (1989) discloses a [$^3$H]-CCP binding assay result of 3.3 μM for the unsubstituted 5-(phosphonomethyl)-phenylalanine compound. Thus, the preferred compound of this invention, 3-(1-naphthalenyl)-5-(phosphonomethyl)-L-phenylalanine, showed at least a ten to thirty fold, and up to a several hundred fold improvement in potency, as measured by binding assays, over NMDA receptor anatgonists in the prior art.

NMDA antagonist activity was determined by functional assays, which included ability of the inventive compounds to prevent the delayed release of lactate dehydrogenase from cultured cortical neurons induced by N-methyl-D-aspartate. The tested inventive compounds also prevented spontaneous epileptiform discharges in a cortical wedge preparation that are evoked through disinhibition of NMDA receptors and NMDA-induced discharges.

Furthermore, the compounds of this invention which have the (S)-configuration of the α-amino acid moiety were found to be a substrate for the neutral amino acid transporter system. Transport capacity was determined by measuring the ability of these compounds to compete with L-phenylalanine for uptake into Chinese hamster ovary (CHO) cells. All transport studies were performed in the presence of 20 μM [$^3$H]-L-phenylalanine and a varying amount of the inventive compound. The capacity of the compound for transport was evaluated by its ability to reduce the transport of phenylalanine. The compounds were determined to be either substrates or not substrates of the neutral amino acid transporter, and have $K_M$ values of between 20 and 500 µM. 3-(1-Naphthalenyl)-5-(phosphonomethyl)-L-phenylalanine inhibited phenylalanine transport in CHO cells.

Furthermore, the compounds of this invention exhibit anticonvulsant activity as indicated in standard tests. The compounds inhibit the electroshock induced convulsions in the mouse [E. Swinyard, J. Am. Pharm. Assoc. Scient. Ed. 38, 201 (1949) and J. Pharmacol. Exp. Ther. 106, 319 (1952)]. In this test, mice received the test substance in a dosage of 0.1–100 mg/kg iv. At a given time (30 sec to 50 min.) following the drug administration, 50 mA, 200 ms long shock was applied with corneal electrodes smeared with electrolyte jelly. This supra-threshold shock produces tonic extensor convulsions of all extremities. Inhibition of the hindlimb extension is taken as a protective action. After investigation of several dose-levels and times, an $ED_{50}$ is estimated. Compounds of this invention have $ED_{50}$'s ranging from 0.5–30 mg/kg.

As a result of their NMDA receptor antagonism the compounds of this invention are useful in the treatment of anxiety, schizophrenia and depression or of CNS degenerative disorders such as Huntington's disease, ALS, Alzheimer's or Parkinson's diseases.

The compounds of this invention protect further against hypoxia-induced degeneration of rat hippocampal neurons in vitro and thus may be useful in disorders arising from cerebral ischemia such as stroke, heart attack or head trauma. They may also be useful in protecting the spinal cord following trauma.

3-(1-Naphthalenyl)-5-(phosphonomethyl)-L-phenylalanine is the most preferred compound of this invention for the prevention of neuronal degeneration. It has an $ED_{50}$ <1 mg/kg in the mouse anticonvulsant model when given iv, and also demonstrates activity after oral administration with an extended duration of action. This preferred compound may be administered at daily dosages from 1 to 500 mg/kg to larger mammals, such as man, or given via other routes of administration, such as iv infusion at 0.1 to 30 mg/kg/hr up to 500 mg/day, in acute neurological disorders.

A further aspect of the present invention is directed to a pharmaceutical composition comprising a pharmaceutical acceptable carrier or diluent and a therapeutically effective amount of a compound of formula I.

For medical use, the amount required of a compound of formula I or pharmacologically acceptable salt thereof—(hereinafter referred to as the active ingredient) to achieve a therapeutic affect will, of course, vary both with the particular compound, the route of administration and the mammal under treatment and the particular disorder or disease concerned. A suitable systemic dose of compound of formula I or pharmacologically acceptable salt thereof for a mammal suffering from, or likely to suffer from any condition as described hereinbefore is in the range of about 0.1 to about 100 mg of base per kilogram body weight, the most preferred dosage being about 1 to about 10 mg/kg of mammal body weight.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate.

While it is possible for an active ingredient to be administered alone, it is preferable to present it as a formulation.

Formulations of the present invention suitable for oral administration may be in the form of discrete units such as capsules, cachets, tablets or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations suitable for parenteral administration conveniently comprise a sterile aqueous preparation of the active ingredient which is preferably isotonic with the blood of the recipient.

Formulations suitable for nasal or buccal administration, (such as self-propelling powder dispensing formulations described hereinafter), may comprise about 0.1% to about 5% w/w, for example 1% w/w of active ingredient.

The formulations for human medical use, of the present invention comprise an active ingredient in association with a pharmaceutically acceptable carrier therefore and optionally other therapeutic ingredient(s). The carrier(s) must be 'acceptable' in the sense of being compatible with the other ingredients of the formulations and not deleterious to the recipient thereof.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose, and/or glycine; b) lubricants, e.g. silica, talcum, stearic acid, its magnesium or calcium salt, and/or polyethyleneglycol; for tablets also; c) binders e.g. magnesium aluminum silicate, starch paste, gelatin, tragacanth, methylcellulose, sodium carboxymethylcellulose and/or polyvinylpyrrolidone; if desired d) disintigrants, e.g. starches, agar, alginic acid, or its sodium salt, or effervescent mixtures; and/or e) absorbents, colorants, flavors, and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain about 0.1 to 75%, preferably about 1 to 50% of the active ingredient.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

The present invention is further directed to a method of prophylactic or therapeutic treatment of cerebral ischemia, cerebral infarction, thromboembolic or hemorrhagic stroke, cerebral vasospasm, hypoglycemia, cardiac arrest, status epilepticus, schizophrenia, epilepsy, neuro-degenerative disorders, Alzheimer's disease, Huntington's disease, or risk of cerebrovascular damage which comprises administering an antagonist effective amount for excitatory amino acid receptors of a compound of the formula I in unit dosage form.

The examples which follow are intended as an illustration of certain preferred embodiments of the invention, and no limitation of the invention is implied.

EXAMPLE 1

Preparation of 1-(3,5-Dimethylphenyl)naphthalene

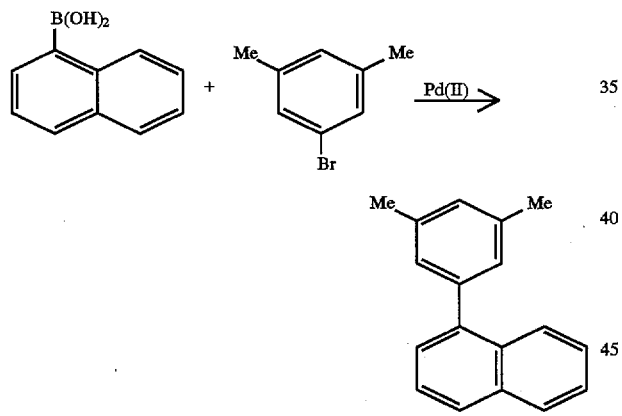

A mixture of dimethyl-5-bromobenzene (1.85 g, 10 mmol), 1-naphthalene boronic acid (1.89 g, 11 mmol), triethylamine (2.8 mL, 20 mmol), tris-(2-tolyl)phosphine (0.125 g, 0.4 mmol), palladium (II) diacetate (0.045 g, 0.4 mmol) and anhydrous dimethylformamide (25 mL) with 5 Å molecular sieves (0.5 g) was stirred at 100° C. under a nitrogen atmosphere for about 4 hours. The solvent was evaporated in vacuo and the residue was treated with 5% aqueous ammonia solution, extracted with ethyl acetate, and washed with saturated aqueous sodium chloride. After filtration to remove a black precipitate, the organic layer was dried over magnesium sulfate, filtered and evaporated. The yellowish oil residue was chromatographed on silica gel (methylene chloride; petroleum ether 1:2 as eluant) to give a colorless oil (1.7 g, 7.3 mmol) in 73% yield. This crystallized upon standing (mp 68°–70° C.).

EXAMPLE 2

Preparation of 2-(3,5-Dimethylphenyl)naphthalene

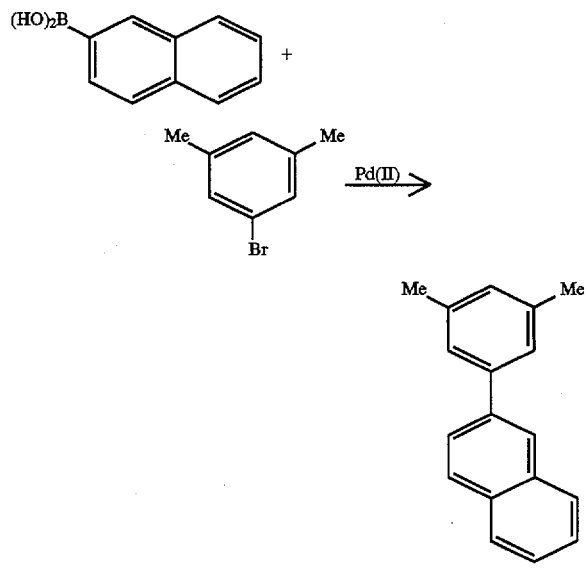

The 2-naphthyl derivative can be prepared using a similar procedure to example 1 except 2-naphthalene boronic acid is used.

EXAMPLE 3

Preparation of 1-[3-(Bromomethyl)-5-methylphenyl]-naphthalene

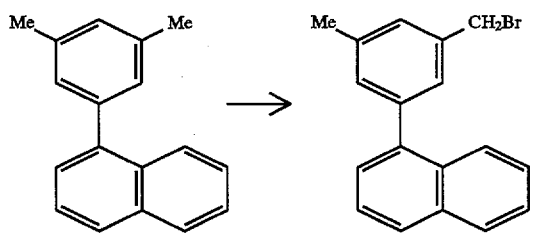

A solution of the biaryl product from example 1 (6.0 g, 25.9 mmol) in 100 mL of carbon tetrachloride was treated with benzoyl peroxide (0.193 g, 0.8 mmol) and the N-bromosuccinimide (4.63 g, 26 mmol). The mixture was refluxed for 40 min and then cooled to 0° C. Precipitated succinimide was removed by filtration. The filtrate was evaporated, and the yellow residue was chromatographed on silica gel (hexane:methylene chloride 5:1 as eluant) to give the starting material and three products. The desired monobromo compound was obtained (4.6 g, 14.79 mmol) in 57% yield.

EXAMPLE 4

Preparation of 2-[3-(Bromomethyl)-5-methylphenyl]-naphthalene

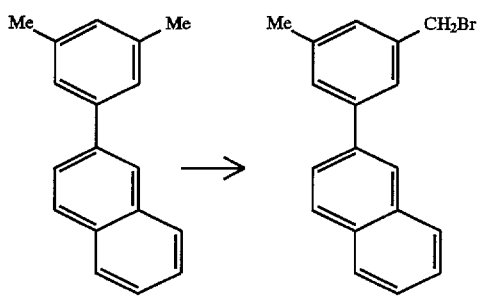

A solution of the 2-naphthyl biaryl product from example 2 is treated in a manner similar to the procedure described in example 3 to obtain the monobromo derivative.

EXAMPLE 5

Preparation of Diethyl [3-methyl-5-(1-naphthalenyl)phenyl] methylphosphonate

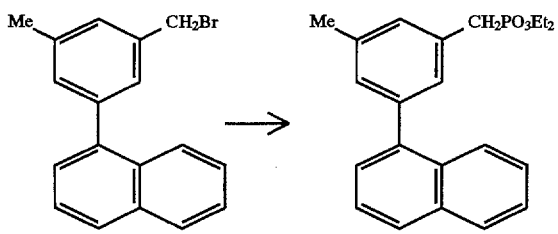

A solution of the bromomethyl adduct from example 3 (4.6 g, 14.8 mmol) in xylene (50 mL) was treated with triethylphosphite (2.7 g, 16.2 mmol) and heated at reflux for about 2 hours. The solvent was evaporated in vacuo and the residue was purified by silica gel chromatography (methylene chloride:ethyl acetate 4:1 as eluant) to give the diethylphosphonate (3.8 g) as a colorless oil in 70% yield.

EXAMPLE 6

Diethyl [3-methyl-5-(2-naphthalenyl)phenyl] methylphosphonate

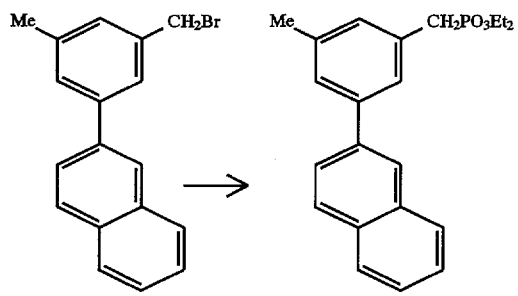

A solution of the monobromo adduct described in example 4 is treated in a similar manner to the procedure described in example 5 to obtain the diethylphosphonate derivative.

EXAMPLE 7

Preparation of Diethyl [3-(bromomethyl)-5-(1-naphthalenyl)phenyl] methylphosphonate

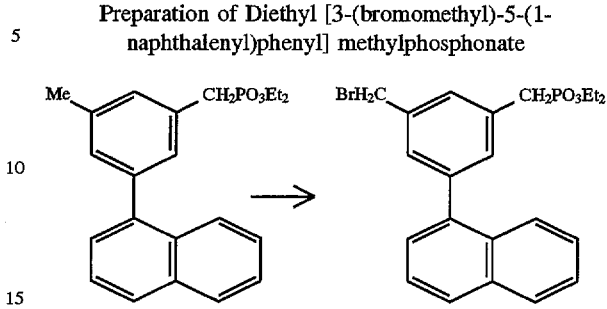

A solution of the phosphonate from example 5 (1.44 g, 3.9 mmol) in carbon tetrachloride (25 mL) was treated with benzoyl peroxide (0.1 g, 0.41 mmol) at room temperature and stirred for 10 min. N-Bromosuccinimide (0.77 g, 4.3 mmol) was then added and the mixture refluxed gently for about 1 hour, and then cooled to 0° C. Succinimide was removed by filtration, and the filtrate was evaporated in vacuo. The residue was chromatographed on silica gel (methylene chloride; ethyl acetate 5:1 as eluant) to give predominantly the monobromo adduct (0.93 g) contaminated with some dibromo derivative (~5% by $^1$H-NMR).

EXAMPLE 8

Preparation of Diethyl [3-bromomethyl)-5-(2-naphthalenyl)phenyl] methylphosphonate

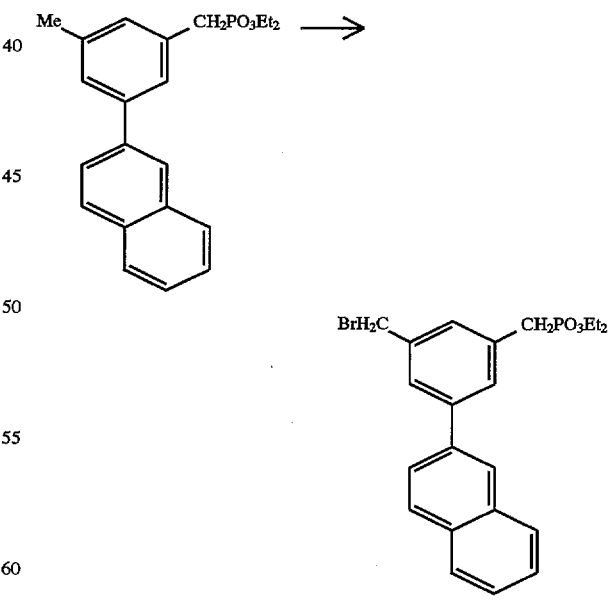

The product described in example 6 is converted to the monobromo adduct by a procedure similar to that used in example 7.

EXAMPLE 9

Preparation of Diethyl (acetylamino)[[3-[(diethoxyphosphinyl)methyl]-5-(1-naphthalenyl)-phenyl] methyl]-propanedioate

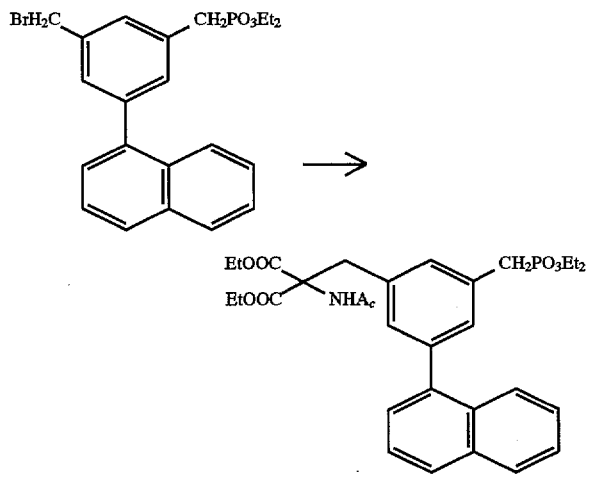

The monobromo adduct from example 7 was dissolved in THF and treated with a THF solution of the sodium salt of diethyl acetamidomalonate (obtained by treatment of diethyl acetamidomalonate with one equivalent of sodium hydride in THF at 0° C. and warmed to room temperature). After stirring for about 4 hours, the mixture was quenched with 10% aqueous HCl, and extracted with diethyl ether several times. The organic layer was dried over magnesium sulfate, filtered and evaporated. The residue was purified by silica gel chromatography.

EXAMPLE 10

Preparation of Diethyl (acetylamino) [[3-[(diethoxyphosphinyl)methyl]-5-(2-naphthalenyl) phenyl]methyl] propanedioate

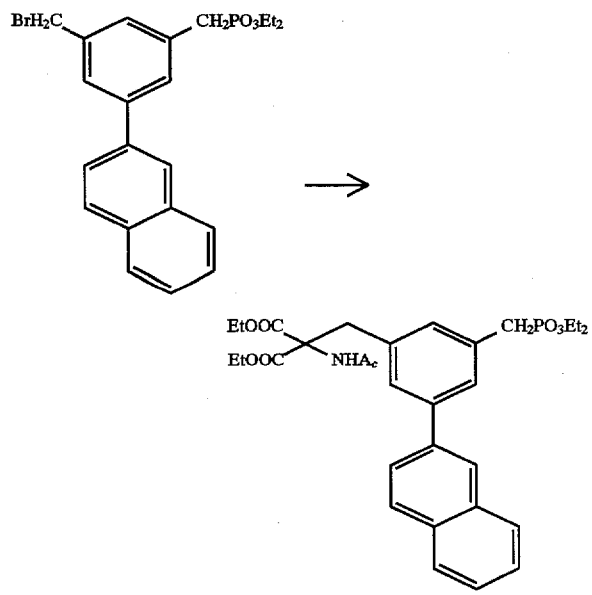

The product described in example 8 is treated with the sodium salt of diethylacetamidomalonate by a procedure similar to that used in example 9 to obtain the fully protected amino acid adduct.

EXAMPLE 11

Preparation of 1,1-Dimethylethyl (2S-trans)-5-[[3-(diethoxyphosphinyl)methyl]-5-(1-naphthalenyl) phenyl]methyl]-2-(1,1-dimethylethyl)-3-methyl-4-oxo-1-imidazolidinecarboxylate

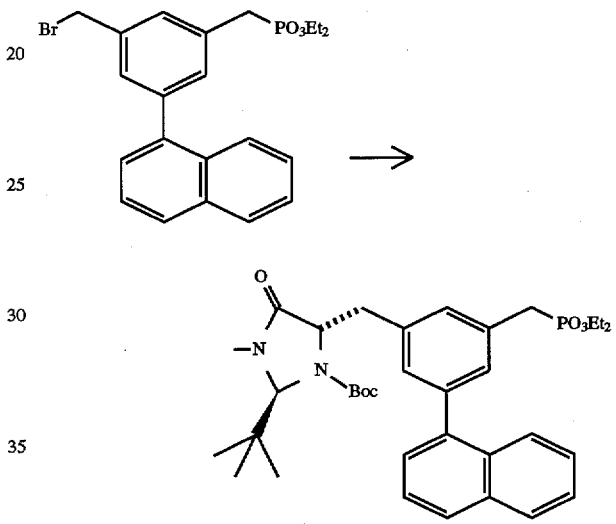

To a solution of diisopropyl amine (0.32 mL, 2.29 mmol) in 10 mL of tetrahydrofuran was added n-butyl lithium (1.43 mL, 1.6M in hexane, 2.29 mmol) at 0° C. over 10 minutes. After stirring for 20 minutes at 0° C., the solution was cooled to −78° C. and a solution of (S)-(−)-1-(t-butoxycarbonyl)-2-t-butyl-3-methyl-4-imidazolidinone (0.586 g, 2.29 mmol) in tetrahydrofuran (5 mL) was added over 20 minutes. The reaction temperature was raised to −20° C. for 30 minutes (light yellow color), recooled to −78° C., and then a solution of product from example 7 (0.93 g, 2.08 mmol) in tetrahydrofuran (5 mL) was added to the reaction mixture over 20 min (orange color). After stirring for about 3 hours, the volume of the mixture was reduced to 3 mL and then poured onto 30 mL of saturated ammonium chloride and extracted with diethyl ether. The organic layer was washed with saturated aqueous sodium chloride, dried over magnesium sulfate, filtered and evaporated. The oil residue was purified by silica gel chromatography (ethyl acetate:methanol 5:1 as eluant) to give the adduct as a colorless oil (0.72 g) in 53% yield. $[\alpha]^{20}+21.9°$ (c 1.6, $CH_2Cl_2$).

EXAMPLE 12

Preparation of 1,1-Dimethylethyl (2S-trans)-5-[[3-(diethoxyphosphinyl)methyl]-5-(2-naphthalenyl)phenyl]methyl]-2-(1,1-dimethylethyl)-3-methyl-4-oxo-1-imidazolidinecarboxylate

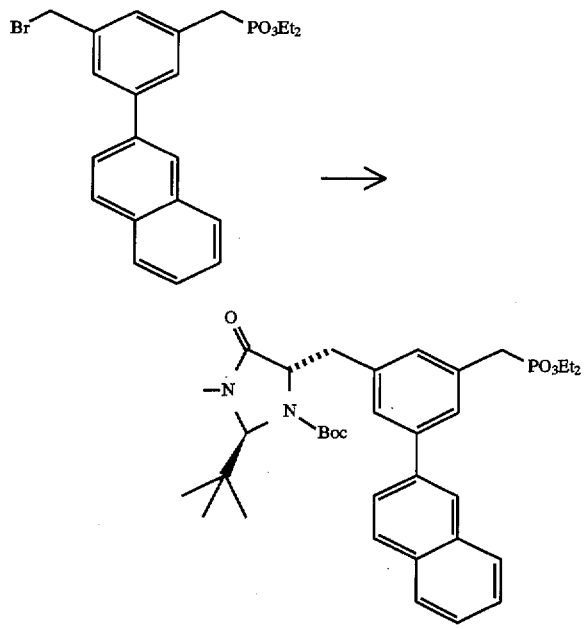

The product described in example 8 is converted to the imidazolidinone adduct by a procedure similar to that used in example 11.

EXAMPLE 13

Preparation of 3-(1-Naphthalenyl)-5-(phosphonomethyl)-L-phenylalanine

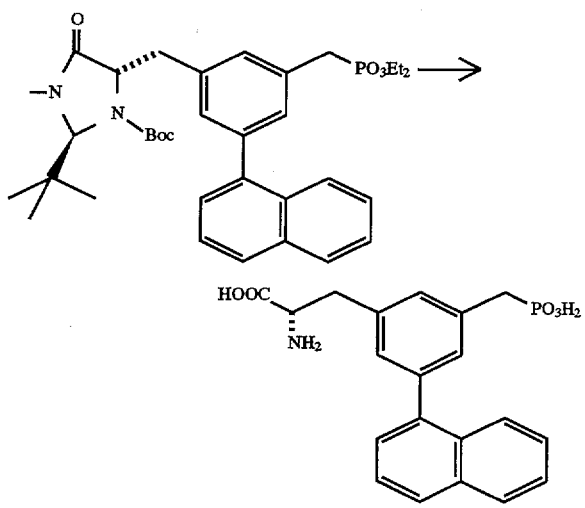

A solution of the imidazolidinone adduct from example 11 in 6N HCl (20 mL) was refluxed for about 24 hours. After cooling, Dowex 50 W×4 resin (5 g) was added to the reaction mixture and the solvent evaporated. The residue/resin was washed in a column sequentially with water (50 mL), ethanol (100 mL), water (50 mL), 5% ammonium hydroxide (100 mL) and 30% ammonium hydroxide (100 mL). The product was identified by C18 reverse phase silica gel tlc plates (water:acetonitrile 1:8) using ninhydrin as a stain. The fractions containing product were combined and evaporated in vacuo (foaming). White powder (mp 262° C., dec.; 285 mg, 0.75 mmol) was obtained in 83% yield after lyophilization. $[\alpha]^{20}-50°$ (c 1.25, $H_2O$).

EXAMPLE 14

Preparation of 3-(2-Naphthalenyl)-5-(phosphonomethyl)-L-phenylalanine

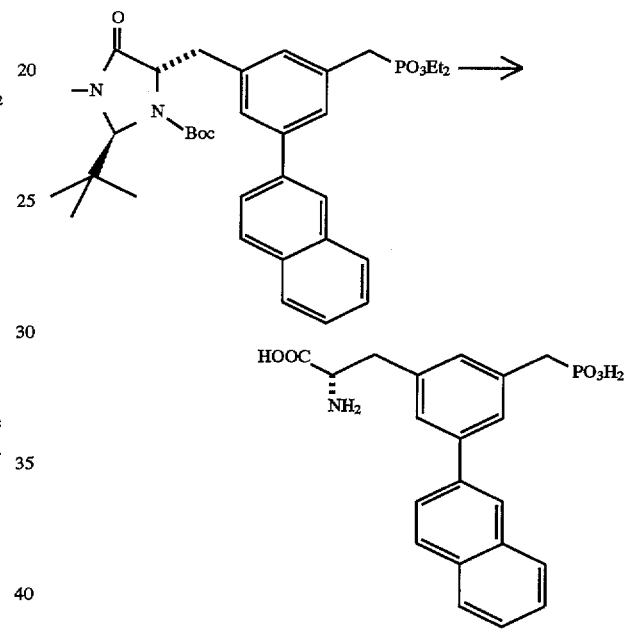

The imidazolidinone adduct described in example 12 is converted to the unprotected amino acid derivative by a procedure similar to that used in example 13.

EXAMPLE 15

Preparation of 3-(1-Naphthalenyl)-5-(phosphonomethyl)-DL-phenylalanine

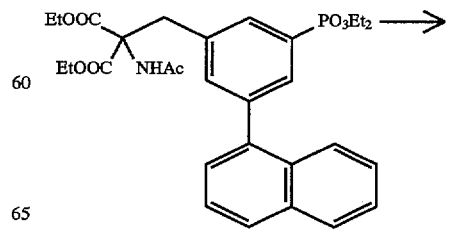

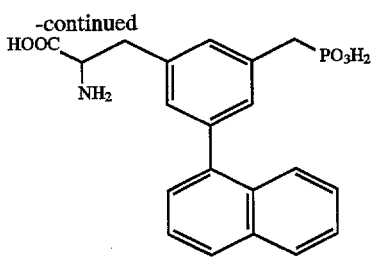

The adduct from example 9 was converted to the racemic, unprotected amino acid derivative by a procedure similar to that used in example 13.

EXAMPLE 16

Preparation of 3-(2-Naphthalenyl)-5-(phosphonomethyl)-DL-phenylalanine

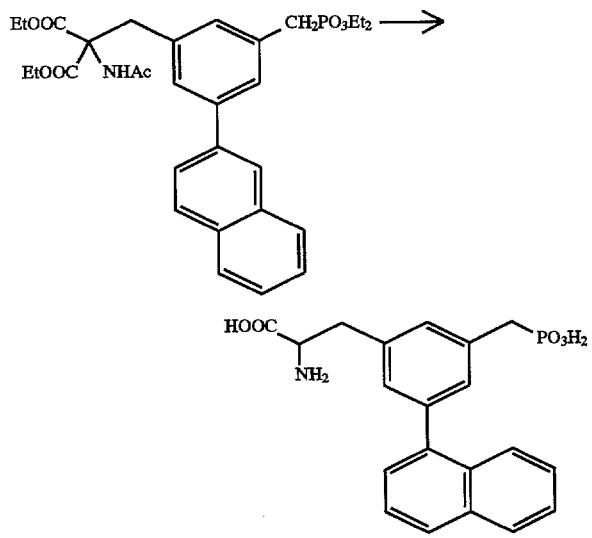

The adduct described in example 10 is converted to the racemic, unprotected amino acid derivative by a procedure similar to that used in example 13.

Other variations and modifications of this invention will be obvious to those skilled in the art.

What is claimed is:

1. A compound represented by the formula:

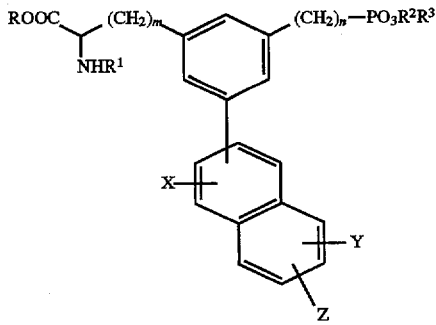

or a pharmaceutically acceptable acid addition, or base salt thereof wherein (a) m and n are independently an integer of 0 to 3; (b) R, $R^2$ and $R^3$ are independently hydrogen or a pharmaceutically acceptable labile ester or amide residue; (c) $R^1$ is hydrogen or a protective group; and (d) X, Y and Z are independently hydrogen, halogen, amino, hydroxy, hydroxyalkyl having 1 to 6 carbon atoms, haloalkyl having 1 to 6 carbon atoms, cyano, nitro, alkyl having 1 to 6 carbon atoms, cycloalkyl, aryl, aralkyl, aminoalkyl having 1 to 6 carbon atoms or alkoxy having 1 to 6 carbon atoms.

2. The compound according to claim 1, wherein R, $R^2$ and $R^3$ are independently hydrogen, lower alkyl, lower alkanoyloxymethyl, di-lower alkylamino-straight chain alkyl of from two to four carbons or pyridylmethyl.

3. The compound according to claim 2, wherein R, $R^2$ and $R^3$ are independently hydrogen or lower alkyl.

4. The compound according to claim 3, wherein m and n are 1.

5. The compound according to claim 4 which is selected from the group consisting of 3-(1-naphthalenyl)-5-(phosphonomethyl)-L-phenylalanine and 3-(2-naphthalenyl)-5-(phosphonomethyl)-L-phenylalanine and pharmaceutically acceptable salts thereof.

6. The compound according to claim 3 which is selected from the group consisting of 3-(1-naphthalenyl)-5-(phosphonomethyl)-DL-phenylalanine, 3-(2-naphthalenyl)-5-(phosphonomethyl)-DL-phenylalanine and pharmaceutically acceptable salts thereof.

7. A pharmaceutical composition useful for treating disorders responsive to the blockade of aspartate or glutamate receptors such as epilepsy, anxiety, schizophrenia, depression, neuropathic pain, CNS degenerative disorders, cerebral hypoxic/ischemic conditions or stress related psychiatric disorders, said composition comprising a pharmaceutically acceptable carrier or diluent and a therapeutically effective amount of at least one compound of claim 1.

8. A method for treating disorders responsive to the blockade of glutamate or aspartate receptors in a human suffering thereof which comprises administering at least one compound of claim 1 in unit dosage form.

9. A method for treating anxiety which comprises administering at least one compound of claim 1 in unit dosage form.

10. A method for treating cerebral hypoxic/ischemia which comprises administering at least one compound of claim 1 in unit dosage form.

11. A method for treating Parkinsonism which comprises administering at least one compound of claim 1 in a unit dosage form.

12. A method for treating anxiety which comprises administering in unit dosage form at least one compound selected from the group consisting of 3-(1-naphthalenyl)-5-(phosphonomethyl)-DL-phenylalanine and 3-(1-naphthalenyl)-5-(phosphonomethyl)-L-phenylalanine.

13. A method for treating cerebral hypoxic/ischemia which comprises administering in unit dosage form at least one compound selected from the group consisting of 3-(1-naphthalenyl)-5-(phosphonomethyl)-DL-phenylalanine and 3-(1-naphthalenyl)-5-(phosphonomethyl)-L-phenylalanine.

14. A method for treating Parkinsonism which comprises administering in unit dosage form at least one compound selected from the group consisting of 3-(1-naphthalenyl)-5-(phosphonomethyl)-DL-phenylalanine and 3-(1-naphthalenyl)-5-(phosphonomethyl)-L-phenylalanine.

* * * * *